(12) United States Patent
Hobbs

(10) Patent No.: US 8,377,986 B2
(45) Date of Patent: Feb. 19, 2013

(54) AMINO ACID DERIVATIVES

(75) Inventor: Christopher Hobbs, London (GB)

(73) Assignee: Proximagen Ltd., London (GB)

( * ) Notice: Subject to any disclaimer, the term of this patent is extended or adjusted under 35 U.S.C. 154(b) by 377 days.

(21) Appl. No.: 12/672,702

(22) PCT Filed: Aug. 4, 2008

(86) PCT No.: PCT/GB2008/002656
§ 371 (c)(1),
(2), (4) Date: Mar. 5, 2010

(87) PCT Pub. No.: WO2009/022098
PCT Pub. Date: Feb. 19, 2009

(65) Prior Publication Data
US 2010/0216878 A1    Aug. 26, 2010

(30) Foreign Application Priority Data
Aug. 11, 2007 (GB) .................................. 0715712.6

(51) Int. Cl.
*A61K 31/24* (2006.01)
*C07C 229/34* (2006.01)
(52) U.S. Cl. ......................................... 514/533; 560/38
(58) Field of Classification Search .................. 514/533; 560/38
See application file for complete search history.

(56) References Cited

U.S. PATENT DOCUMENTS
3,859,331 A    1/1975    Kaiser et al.

FOREIGN PATENT DOCUMENTS
DE    2153800 A1    5/1972

OTHER PUBLICATIONS
International Search Report for PCT/GB2008/002656 dated Dec. 10, 2008.

*Primary Examiner* — Sreeni Padmanabhan
*Assistant Examiner* — Sahar Javanmard
(74) *Attorney, Agent, or Firm* — Banner & Witcoff, Ltd.

(57) ABSTRACT

The compound 3,3-dimethyl-butyric acid 4-((S)-2-amino-2-methoxycarbonyl-ethyl)-2-(3,3-dimethyl-butyryloxy)-phenyl ester of formula (I) has dopaminergic properties.

4 Claims, No Drawings

AMINO ACID DERIVATIVES

CROSS REFERENCE TO RELATED APPLICATIONS

This application is a National Stage application of co-pending PCT application PCT/GB2008/002656 filed Aug. 4, 2008, which claims the benefit of Great Britain application number 0715712.6 filed Aug. 11, 2007. These applications are incorporated herein by reference in their entireties.

The present invention relates to a compound which diminishes the symptoms of dopamine deficiency. In particular, the invention relates to a compound which is a prodrug of L-dopa (levodopa; 3-hydroxy-L-tyrosine) which is converted in vivo to L-dopa resulting in prolonged, effective exposure to that drug.

BACKGROUND TO THE INVENTION

Dopamine is a substance produced naturally by neurons in the basal ganglia of the brain that allows smooth, co-ordinated control of voluntary movement. Loss of, or impairment of, dopamine-producing neurons in the brain is implicated in Parkinson's disease and related parkinson-plus syndromes. These conditions respond to dopamine replacement therapy. Other conditions, for example, Restless Legs Syndrome (RLS) also respond to dopamine replacement therapy.

RLS is a neurosensorimotor disorder with parestethasias, sleep disturbances and, in most cases, periodic limb movements of sleep (PLMS). Two forms of RLS appear to exist: the idiopathic and the uremic form. RLS is characterised by (1) a desire to move the legs, usually associated with paresthesias/dysesthesias, (2) motor restlessness, (3) worsening or exclusive presence of symptoms at rest (i.e. lying, sitting) with at least partial or temporary relief by activity, and (4) worsening of symptoms during the evening or night.

Parkinson's disease is a progressive neurodegenerative disorder that affects neuronal cells in the substantia nigra in the mid-brain. It is an age-related disorder of the central nervous system primarily attacking people over the age of 60. Approximately one out of every 500 people contract the illness and approximately one out of every 100 people over the age of 60 develop the illness. As indicated above, Parkinson's Disease is thought to be caused by a deficiency of dopamine. The common symptoms include tremor, stiffness (or rigidity) of muscles, slowness of movement (bradykinesia) and loss of balance (postural dysfunction). Parkinson's Disease is one of the most prevalent neurodegenerative illnesses. The natural history of the disease is progressive and from 10-15 years from onset of the disease becomes disabling in most patients.

Parkinson's disease is largely sporadic and referred to as idiopathic in nature. Forms of the illness due to vascular incidents and to toxin exposure also exist. Rare familial forms of the illness also exist.

Many treatments have been tried since James Parkinson first described the condition in 1817. Current therapy for Parkinson's disease is based on dopamine replacement therapy based on the use of the dopamine precursor levodopa (or L-dopa) or dopaminergic compounds. L-dopa is highly effective in reversing the motor symptoms of the illness but on chronic treatment and with disease progression, its effectiveness declines. The duration of drug response is reduced and unpredictable fluctuations in movement occur. Treatment is associated with therapy limiting side effects which include involuntary movements (dyskinesia) and psychosis.

There is therefore a need for L-dopa prodrugs for use in dopamine deficiency diseases, which are converted in vivo to L-dopa and result in prolonged, effective exposure to L-dopa, thereby prolonging the response to the drug.

BRIEF DESCRIPTION OF THE INVENTION

Several classes of potential prodrugs of L-dopa have been proposed. One proposed class, of which several specific members are known from the patent and scientific literature consists of compounds of formula (IA):

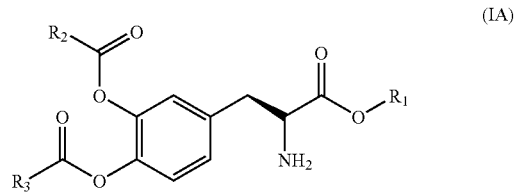

(IA)

wherein $R_1$, $R_2$, and $R_3$ are alkyl. This invention relates to 3,3-dimethyl-butyric acid 4-((S)-2-amino-2-methoxycarbonyl-ethyl)-2-(3,3-dimethyl-butyryloxy)-phenyl ester—a novel member of the class of compounds (IA), which on administration produces longer circulating levels of L-dopa that other, structurally similar, members of the class.

DETAILED DESCRIPTION OF THE INVENTION

According to the invention, there is provided the compound 3,3-dimethyl-butyric acid 4-((S)-2-amino-2-methoxy-carbonyl-ethyl)-2-(3,3-dimethyl-butyryloxy)-phenyl ester of formula (I)

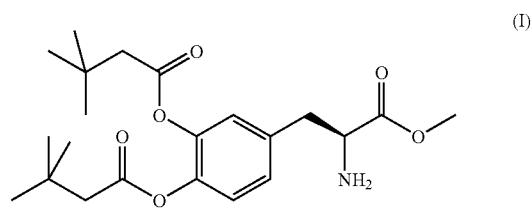 [SMILES: COC(=O)[C@@H](N)Cc1ccc(OC(=O)CC(C)(C)C)c(OC(=O)CC(C)(C)C)c1]

(I)

The compound (I) of the invention may be prepared in the form of salts, especially pharmaceutically acceptable salts, hydrates, and solvates thereof. Any claim or reference herein to "the compound (I)", "the present compound", "the compound of the invention", "the compound with which the invention is concerned", or "the compound of formula (I)", and the like, includes salts, hydrates, and solvates of such compounds.

As used herein the term "salt" includes acid addition salts. Such salts, including pharmaceutically acceptable salts, may be formed with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like. For a review on suitable salts, see *Handbook of Pharmaceutical Salts: Properties, Selection, and Use* by Stahl and Wermuth (Wiley-VCH, Weinheim, Germany, 2002).

The compound of the invention is cleaved in the body to release L-dopa or L-dopa precursors. L-dopa itself is metabolised in the gut, the gut membrane, plasma, kidney and the liver and this significantly reduces its bioavailability and increases intersubject variability in the resulting blood levels of L-dopa. The present compound have a more favourable pharmacokinetic profile than L-dopa itself, and other L-dopa prodrugs of the generally known class (IA) above, due to the time over which cleavage occurs and L-dopa is released.

Hence the compound of the invention is useful in a method of treatment of a condition associated with impaired dopaminergic signaling in a subject, comprising administering to the subject an amount of the compound effective to reduce such impairment. The compound is also useful in the preparation of a composition for treatment of a condition associated with impaired dopaminergic signaling. Examples of such conditions include Parkinson's disease, or Restless Legs Syndrome, as well as Tourette's syndrome, attention deficit hyperactive disorder, generation of pituitary tumours, a parkinson-plus syndrome, levodopa responsive dystonia, dyskinesia, periodic movements in sleep, dysphagia or neuroleptic malignant syndrome.

Typical examples of Parkinson's disease which can be treated with the compounds of the invention include sporadic Parkinson's disease, familial forms of Parkinson's disease and post-encephalitic Parkinsonism.

Typical examples of Parkinson-plus syndromes which can be treated with the compounds of the invention include progressive supranuclear palsy and multiple system atrophy.

Typically, the dyskinesia is L-dopa-induced dyskinesia.

The compounds of the invention may be administered in a variety of dosage forms. Thus, they can be administered orally, for example as tablets, capsules including capsules containing the active ingredient in solid or liquid form), troches, lozenges, aqueous or oily suspensions, dispersible powders or granules. The compounds can be administered in a sublingual formulation, for example a buccal formulation. The compounds of the invention may also be administered parenterally, whether subcutaneously, intravenously, intramuscularly, intrasternally, transdermally, by inhalation, intranasally, or by infusion techniques. The compounds may also be administered as suppositories. Thus, the compounds of the invention are administered orally, or by inhalation, or intranasally, but preferably the compounds of the invention are administered orally and more preferably, the compounds of the invention are administered as a tablet or capsule. In the latter connection, administration of the compounds in a hard gelatine capsule form, or in one of the many sustained release formulations known in the art will often be preferred.

The present invention further provides a pharmaceutical composition containing the compound of formula (I) as defined above, and a pharmaceutically acceptable carrier.

The compound of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol. Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Since the compound of the invention is preferably administered orally, the present invention further provides a pharmaceutical composition containing a compound of formula (I) as defined above, and a pharmaceutically acceptable carrier in the form of a capsule, tablet or orally administrable liquid formulation, for example an aqueous formulation prepared ad hoc by dissolving a solid tablet containing the compound of the invention and an effervescent couple.

Solutions for injection or infusion may contain as carrier, for example, sterile water or preferably they may be in the form of sterile, aqueous, isotonic saline solutions.

The compounds of the present invention may also be administered with other active compounds which have previously been shown to be beneficial in L-dopa therapy, and may also be administered together with L-dopa itself. For example, L-dopa has previously been co-administered with peripheral decarboxylase inhibitors and with catechol-O-methyltransferase (COMT) inhibitors. The present invention therefore provides a pharmaceutical composition containing a compound of the invention or a pharmaceutically acceptable salt thereof as defined above, a peripheral decarboxylase inhibitor and/or a COMT inhibitor, and a pharmaceutically acceptable carrier or diluent. A suitable decarboxylase inhibitor is carbidopa or benserazide. Preferably the peripheral decarboxylase inhibitor is carbidopa. A suitable COMT inhibitor is entacapone.

Also provided is a product comprising (a) a compound of the invention or a pharmaceutically acceptable salt thereof as defined above and (b) a peripheral decarboxylase inhibitor and/or (c) a COMT inhibitor, for simultaneous separate or sequential use in the treatment of the human or animal body.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial. However, it is expected that a typical dose will be in the range from about 0.001 to 50 mg per kg of body weight.

The compound of the invention and its hydrochloride salt may be prepared as described below. Other salt forms may be prepared by analogous methods or by recovery from other inorganic or organic acid solutions.

Preparation of the Compound (I) and Structurally Related Comparison Compounds

HPLC/MS data was obtained using an HP1100 LC combined with a Waters Micromass ZMD mass spectrometer operating in positive ion mode. A Genesis 4 micron C18 column was used and samples were eluted with a gradient made up from two solvents: 0.1% aqueous formic acid and 0.1% formic acid/acetonitrile. The gradient rose from 5% acetonitrile to 95% over a period of 7 minutes and was held at 95% for 3 minutes before dropping to 5% over 4 minutes.

MASS SPECTRUM was obtained with a VG Bio-Q instrument with Z spray operating in positive ion mode.

Compound (I)

3,3-Dimethyl-butyric acid 5-((S)-2-tert-butoxycarbonylamino-2-methoxy-carbonyl-ethyl)-2-(3,3-dimethyl-butyryloxy)-phenyl Ester (S)-2-tert-Butoxycarbonylamino-3-(3,4-dihydroxy-phenyl)-propionic acid methyl ester (311 mg) was partly dissolved in dichloromethane (5 ml) and t-butylacetyl chloride (0.35 ml) added. Triethylamine (0.35 ml) was then added followed by a catalytic amount of 4-N,N-Dimethylaminopyridine. The mixture was stirred and heated at 50 C for 7 hr. The reaction mixture was diluted with water and dichloromethane. The organic phase was washed with dil HCl, aq NaHCO$_3$ and with brine. Drying (MgSO$_4$) and evaporation gave the crude product which was purified by silica gel chromatography eluting with mixtures of ethyl acetate-hexane. 3,3-Dimethyl-butyric acid 5-((S)-2-tert-butoxycarbonylamino-2-methoxycarbonyl-ethyl)-2-(3,3-dimethyl-butyryloxy)-phenyl ester was obtained as a pale yellow oil, 375 mg; Rf 0.36 (ethyl acetate-hexane 1:3); HPLC/MS retention time 7.59 min, m/z 508 (MH$^+$).

Compound (I) as the Hydrochloride Salt (S)-2-[3,4-Bis-(3,3-dimethyl-butyryloxy)-phenyl]-1-methoxycarbonyl-ethyl-ammonium; Chloride

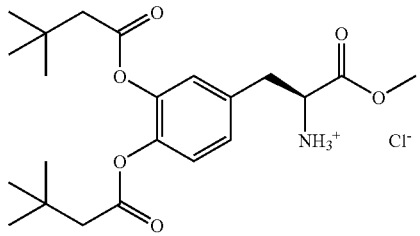 [SMILES: COC(=O)[C@@H]([NH3+])Cc1ccc(OC(=O)CC(C)(C)C)c(OC(=O)CC(C)(C)C)c1 ; [Cl-]]

3,3-Dimethyl-butyric acid 5-((S)-2-tert-butoxycarbonylamino-2-methoxycarbonyl-ethyl)-2-(3,3-dimethyl-butyryloxy)-phenyl ester (350 mg) was dissolved in 4M HCl in dioxane (5 ml) and the solution was left at room temperature for ca 1.5 hr. Evaporation of solvent gave an oil which was redissolved in ether and evaporated to dryness again giving (S)-2-[3,4-bis-(3,3-dimethyl-butyryloxy)-phenyl]-1-methoxycarbonyl-ethyl-ammonium chloride as a solid, 225 mg; NMR (500 MHz, d$_6$ DMSO) 1.06 and 1.07 (together 18H, two s), 2.43 (ca 4H, s), 3.11 (1H, dd J 14, 7), 3.18 (1H, dd J 14, 5), 3.68 (3H, s), 4.31 (1H, br t), 7.13-7.22 (3H, m), 8.6 (ca 3H, br s exch D$_2$O); MS m/z 408 (MH$^+$).

Preparation of Structurally Similar Comparison Compounds

Comparison compounds (II-VII) in Table 1 below, which are structurally similar to the compound of the invention in that they are all members of the same L-dopa prodrug class (IA) above, were prepared by methods directly analogous to those described above for the preparation of compound (I) as the hydrochloride salt.

Biological Results

The compound of the invention (I) and comparison compounds (II-VII) were tested in an assay which measures parameters relevant to the pharmacokinetic profile of the test compound. The assay measured the length of time L-dopa remained in the blood of test animals Pharmacokinetic Analysis Pharmacokinetics Dosing Protocol Naïve male Wistar rats (bodyweight=250-500 g) were used for the pharmacokinetic studies. Animals were fasted overnight. The compound of interest was dissolved in 0.9% saline and co-dosed with Benserazide (10 mg/kg) at a molecular weight equivalent dose to 12.5 mg/kg L-Dopa. Blood samples were taken via a butterfly needle located into the lateral tail vein and collected into sample tubes containing heparin as the anti-coagulant. Blood samples were centrifuged at 5000 rpm for 10 minutes; the supernatant plasma was removed and stored at −80° C.

Preparation of Sample and Standard Solutions

Stock solutions of 10 mM L-Dopa and Warfarin were prepared in 20% TFA, 10 mM sodium meta bisulphite and DMSO, respectively.

Standard curves and Quality control (QC) samples were prepared by spiking control rat plasma with L-Dopa to achieve an initial concentration of 50 μM. Serial dilutions of this solution were performed in rat plasma to result in solutions with 25, 6.25, 3.125, 1.56, 0.78 and 0.39 μM L-Dopa.

One volume of sample plasma, standard and QC sample plasma was transferred from each sample vial to a 96 well plate. Compounds were extracted from plasma by addition of one volume of 20% TFA in 10 mM sodium meta bisulphite containing the internal standard, Warfarin, at 0.5 μM. The samples were vortex mixed and centrifuged at 4500 rpm for 4 minutes to precipitate plasma proteins. One volume of water was added to each well and the protein pellet was re-suspended. The samples were again vortex mixed and centrifuged at 4500 rpm for 9 minutes to precipitate plasma proteins.

The supernatant was analysed as detailed below.

LC-MS/MS Analysis

The LC-MS/MS system consisted of an Agilent 1100 series gradient HPLC pump (Agilent Technologies, Palo Alto, Calif.), a CTC HTS PAL Autosampler (CTC Analytics, Zwingen, Switzerland) and an Applied Biosystems/MDS Sciex API 3000 triple quadrupole mass spectrometer (Applied Biosystems, Foster City, Calif.) equipped with a turbo ionspray interface and operated in positive electrospray mode. Analytes in incubation mixtures were separated by reverse phase HPLC using a Phenomenex Sphereclone ODS 2 column (150×4.6 mm, 3 μm, Phenomenex, Torrance, Calif.).

A gradient elution program was used at a flow rate of 1 ml/min with a mobile phase consisting of acetonitrile/0.1% formic acid (5% v/v) in water/0.1% formic acid, delivered for 1.5 minutes, after which time the acetonitrile concentration was increased to 95% over 0.5 minutes and held at 95% for four minutes before restoring it back to 5% for the remaining two minutes. The injection volume was 20 μl. Approximately 10% of the eluent was introduced into the mass spectrometer source. The source temperature of the mass spectrometer was maintained at 450° C., and other source parameters (e.g., collision energy, declustering potential, curtain gas pressure etc.) were optimised on the day of analysis to achieve maximum sensitivity. Quantification of L-Dopa and Warfarin was achieved by monitoring the transitions of m/z=198.075/152.1 and m/z=369.069/163, respectively.

The apparent half-life of the L-Dopa generated from the prodrugs was calculated from the terminal plasma samples using non compartment models of WinNonLin (Pharsight California USA) with no weighting.

Results:

Comparison of the apparent half-life of (S)-2-[3,4-Bis-(3,3-dimethyl-butyryloxy)-phenyl]-1-methoxycarbonyl-ethyl-ammonium chloride (compound I) with other close structural analogues, including the most similar compounds previously described in the prior art, surprisingly shows that the apparent half-life of compound (I) is significantly greater than the structurally analogous comparison compounds.

| Structure | Compound | t1/2 app L-Dopa (min) |
| --- | --- | --- |
| 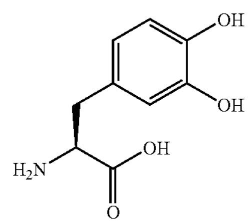 [SMILES: N[C@@H](Cc1ccc(O)c(O)c1)C(=O)O] | L-Dopa | 89.3 |
| 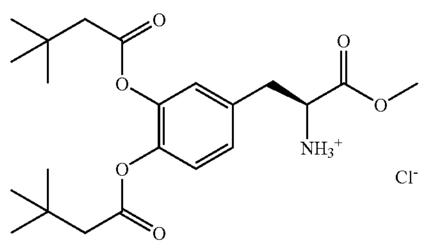 [SMILES: COC(=O)[C@@H]([NH3+])Cc1ccc(OC(=O)CC(C)(C)C)c(OC(=O)CC(C)(C)C)c1 ; [Cl-]] | I | 141.7 |
| 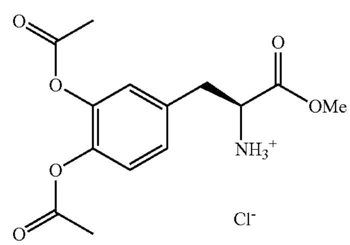 [SMILES: COC(=O)[C@@H]([NH3+])Cc1ccc(OC(C)=O)c(OC(C)=O)c1 ; [Cl-]] | II | 89.7 |
| 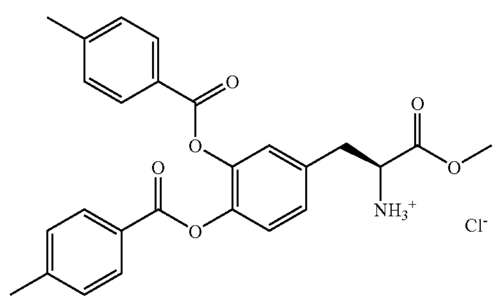 | III | 72.3 |
| 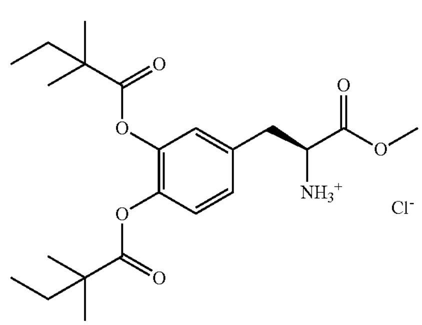 [SMILES: CCC(C)(C)C(=O)Oc1ccc(C[C@H]([NH3+])C(=O)OC)cc1OC(=O)C(C)(C)CC ; [Cl-]] | IV | 102.7 |

| Structure | Compound | t1/2 app L-Dopa (min) |
|---|---|---|
| 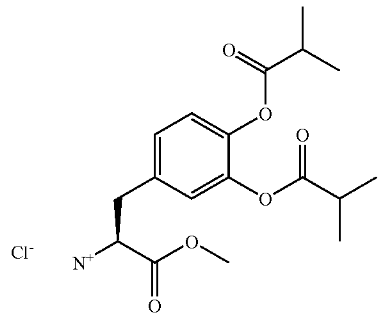 [SMILES: [Cl-] ; COC(=O)[C@@H]([NH3+])Cc1ccc(OC(=O)C(C)C)c(OC(=O)C(C)C)c1] | V | 83.2 |
| 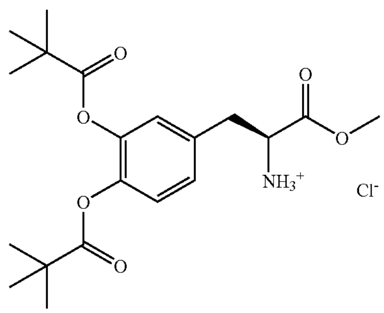 [SMILES: COC(=O)[C@@H]([NH3+])Cc1ccc(OC(=O)C(C)(C)C)c(OC(=O)C(C)(C)C)c1 ; [Cl-]] | VI | 77.2 |
| 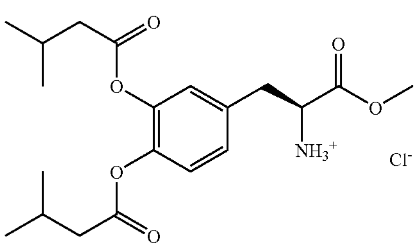 [SMILES: COC(=O)[C@@H]([NH3+])Cc1ccc(OC(=O)CC(C)C)c(OC(=O)CC(C)C)c1 ; [Cl-]] | VII | 69.9 |

The invention claimed is:

1. The compound 3,3-dimethyl-butyric acid 4-(S)-2-amino-2-methoxycarbonyl-ethyl)-2-(3,3-dimethyl-butyryloxy)-phenyl ester of formula (I)

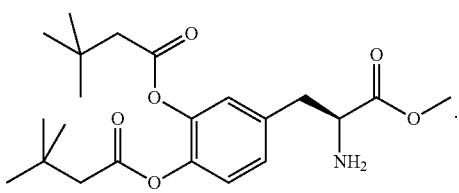

(I)

2. The compound as claimed in claim 1 wherein the compound is in the form of a pharmaceutically acceptable salt.

3. A pharmaceutical composition comprising the compound as claimed in claim 1 together with a pharmaceutically acceptable carrier.

4. A pharmaceutical composition comprising the compound as claimed in claim 2 together with a pharmaceutically acceptable carrier.

* * * * *

UNITED STATES PATENT AND TRADEMARK OFFICE
CERTIFICATE OF CORRECTION

PATENT NO. : 8,377,986 B2  Page 1 of 1
APPLICATION NO. : 12/672702
DATED : February 19, 2013
INVENTOR(S) : Christopher Hobbs It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 400 days.

Signed and Sealed this
First Day of September, 2015

Michelle K. Lee
*Director of the United States Patent and Trademark Office*